United States Patent [19]

Leyendecker et al.

[11] Patent Number: 5,112,823
[45] Date of Patent: May 12, 1992

[54] 3(2H)-PYRIDAZINONE DERIVATIVES AND THE USE THEREOF FOR CONTROLLING PESTS

[75] Inventors: Joachim Leyendecker, Ladenburg; Hans-Juergen Neubauer, Muenster-Hiltrup; Uwe Kardorff, Mannheim; Thomas Kuekenhoehner, Frankenthal; Christoph Kuenast, Otterstadt; Peter Hofmeister, Neustadt, all of Fed. Rep. of Germany

[73] Assignee: BASF Aktiengesellschaft, Ludwigshafen, Fed. Rep. of Germany

[21] Appl. No.: 508,206

[22] Filed: Apr. 12, 1990

[30] Foreign Application Priority Data

Apr. 29, 1989 [DE] Fed. Rep. of Germany ....... 3914337

[51] Int. Cl.⁵ .............................................. C07D 237/16
[52] U.S. Cl. ...................................... 514/252; 544/238
[58] Field of Search ...................... 544/238; 514/252

[56] References Cited

U.S. PATENT DOCUMENTS

| 4,837,217 | 6/1989 | Ogura et al. | 544/238 |
| 4,910,201 | 3/1990 | Kawamura et al. | 544/238 |
| 4,929,617 | 5/1990 | Leyendecker et al. | 544/238 |
| 4,945,091 | 7/1990 | Makabe et al. | 514/252 |
| 4,992,456 | 2/1991 | Diehr | 544/238 |

FOREIGN PATENT DOCUMENTS

| 0199281 | 10/1986 | European Pat. Off. . |
| 0302346 | 2/1989 | European Pat. Off. . |
| 0320733 | 6/1989 | European Pat. Off. . |
| 0275569 | 11/1988 | Japan | 544/238 |

Primary Examiner—Donald G. Daus
Attorney, Agent, or Firm—Keil & Weinkauf

[57] ABSTRACT

3(2H)-Pyridazinone derivatives of the general formula I

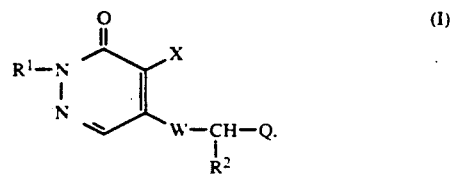

where $R^1$ is $C_1$-$C_8$-alkyl, $R^2$ is hydrogen or $C_1$-$C_4$-alkyl, X is halogen, W is oxygen or sulfur, and Q is a substituted or unsubstituted, 5- or 6-membered heterocyclic structure having 2 to 4 heteroatoms selected from the group consisting of nitrogen, oxygen and sulfur, with the proviso that Q is not isoxazolyl or pyridazinyl, and their use as pesticides.

5 Claims, No Drawings

3(2H)-PYRIDAZINONE DERIVATIVES AND THE USE THEREOF FOR CONTROLLING PESTS

The present invention relates to novel 3(2H)-pyridazinone derivatives of the general formula I

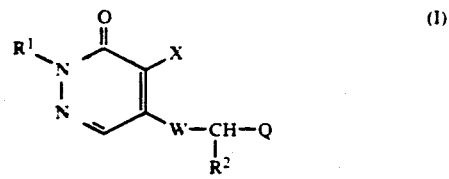

where $R^1$ is $C_1-C_8$-alkyl, $R^2$ is hydrogen or $C_1-C_4$-alkyl, X is halogen, W is oxygen or sulfur and Q is a 5- or 6-membered heterocycle which has 2 to 4 hetero atoms from the group comprising nitrogen, oxygen or sulfur and which is unsubstituted or substituted one to three times by halogen, $C_1-C_8$-alkyl, $C_2-C_6$-alkenyl, $C_2-C_4$-alkynyl, $C_1-C_4$-haloalkyl, $C_1-C_8$-alkoxyy, $C_2-C_8$-alkoxyalkyl, $C_3-C_8$-cycloalkyl, cyano, nitro, aryl and $C_7-C_{20}$-aralkyl, which are unsubstituted or substituted one to three times by halogen, $C_1-C_8$-alkyl, $C_1-C_8$-alkoxy, $C_1-C_4$-haloalkyl, $C_1-C_4$-haloalkoxy, cyano or nitro, with the proviso that Q is not isoxazolyl or pyridazinyl, and salts which are tolerated by plants of the 3(2H)-pyridazinone derivatives I.

The present invention additionally relates to pest-control agents which contain the compounds I as active ingredients, and to a method for controlling pests.

The older German Patent Applications P 37 42 266.9 (EP-A-320 733) (U.S. Pat. No. 4,929,617) and P 38 44 227.2 describe 5-isoxazolylmethyl-3(2H)-pyridazinones. Furthermore, EP-A-199 281 (U.S. Pat. No. 4,837,217) discloses a large number of 3(2H)-pyridazinones substituted by hetaryl radicals, but the latter comprise only those of pyrrole, furan, thiophene, pyridine and pyridazine. EP-A-302,346 (U.S. Pat. No. 4,945,091) likewise describes a large number of 3(2H)-pyridazinones substituted by hetaryl radicals, but they contain no $C_1-C_8$-alkyl as $R^1$.

Because the insecticidal and acaricidal action of the compounds described above is not always satisfactory, the object of the present invention was to provide novel 3(2H)-pyridazinone derivatives which are substituted by hetaryl radicals and have an improved action.

Accordingly, we have found the novel 3(2H)-pyridazinone derivatives of the general formula I defined above, and a process for the preparation thereof. We have furthermore found that the compounds I are outstandingly suitable for controlling pests, while being very well tolerated by plants.

Specific meanings of the substituents in the formula I are as follows:

$R^1$ is unbranched or branched $C_1-C_8$-alkyl, preferably $C_1-C_6$-alkyl, particularly preferably $C_1-C_4$-alkyl, such as methyl, ethyl, n-propyl, iso-propyl, n-butyl, iso-butyl, sec-butyl and tert-butyl, $R^2$ is hydrogen, unbranched or branched $C_1-C_4$-alkyl as listed for $R^1$, preferably $C_1-C_2$-alkyl, particularly preferably methyl, X is halogen, preferably chlorine or bromine, particularly preferably chlorine, W is oxygen or sulfur, particularly preferably sulfur, Q is a 5- or 6-membered heterocycle which has 2 to 4, in particular 2 to 3, hetero atoms such as nitrogen, oxygen or sulfur and is unsubstituted or substituted one to three times, preference being given to pyrazole, imidazole, 1,2,4-triazole, isothiazole, oxazole, thiazole, 1,3,4-oxadiazole, 1,3,4-thiadiazole, 1,2,4-oxadiazole, pyrimidine, pyrazine, 1,3,5-triazine, 1,2,3-triazine and 1,2,4-triazine, and particular preference being given to pyrazole, imidazole, 1,2,4-triazole, isothiazole, oxazole, thiazole, 1,3,4-oxadiazole, 1,3,4-thiadiazole, 1,2,4-oxadiazole, 1,2,4-thiadiazole, pyrimidine and pyrazine, and suitable substituents being the following: halogen, preferably fluorine, chlorine and bromine, particularly preferably fluorine and chlorine, $C_1-C_8$-alkyl, preferably $C_1-C_4$-alkyl, particularly preferably methyl, ethyl, iso-propyl and tert-butyl, $C_2-C_8$-alkenyl, preferably $C_2-C_4$-alkenyl, particularly preferably ethenyl, 1-methylethenyl, propenyl and 2-methylpropenyl, $C_1-C_4$-haloalkyl, preferably $C_1-C_2$-haloalkyl which is substituted by fluorine and/or chlorine, particularly preferably trifluoromethyl, 2,2,2-trifluoroethyl and trichloromethyl, $C_1-C_8$-alkoxy, preferably $C_1-C_3$-alkoxy, particularly preferably methoxy, ethoxy, n-propyloxy and iso-propyloxy, $C_2-C_8$-alkoxyalkyl, preferably $C_2-C_4$-alkoxyalkyl, particularly preferably methoxymethyl, 1-methoxyethyl, 2-methoxyethyl and 1-methoxypropyl, $C_3-C_8$-cycloalkyl, preferably $C_3-C_5$-cycloalkyl such as cyclopropyl, cyclobutyl and cyclopentyl, cyano, nitro, aryl, preferably phenyl and naphthyl, particularly preferably phenyl, $C_7-C_{20}$-aralkyl preferably $C_7-C_{12}$-phenylalkyl, particularly preferably benzyl and phenethyl.

The aryl and $C_7-C_{20}$-aralkyl radicals are unsubstituted or substituted one to three times by:

halogen, preferably fluorine, chlorine and bromine, particularly preferably fluorine and chlorine, $C_1-C_8$-alkyl, preferably $C_1-C_6$-alkyl, particularly preferably $C_1-C_4$-alkyl, such as methyl, ethyl, n-propyl, isopropyl, n-butyl, iso-butyl, sec-butyl and tert-butyl, $C_1-C_8$-alkoxy, preferably $C_1-C_6$-alkoxy, particularly preferably $C_1-C_4$-alkoxy, such as methoxy, ethoxy, n-propyloxy, iso-propyloxy, n-butyloxy, iso-butyloxy, sec-butyloxy and tert-butyloxy, $C_1-C_4$-haloalkyl, preferably fluoro- and/or chloro-$C_1-C_3$-alkyl, particularly preferably fluoro- and/or chloro-$C_1-C_2$-alkyl, such as fluoromethyl, difluoromethyl, trifluoromethyl, chloromethyl, dichloromethyl, trichloromethyl, chlorofluoromethyl, chlorodifluoromethyl, dichlorofluoromethyl, 1,1,2,2-tetrafluoroethyl, 1,2,2,2-tetrafluoroethyl, 1,1,2,2-tetrachloroethyl and 1,2,2,2-tetrachloroethyl, $C_1-C_4$-haloalkoxy, preferably fluoro- and/or chloro-$C_1-C_3$-alkoxy, particularly preferably fluoro- and/or chloro-$C_1-C_2$-alkoxy, such as fluoromethoxy, difluoromethoxy, trifluoromethoxy, chloromethoxy, dichloromethoxy, trichloromethoxy, chlorofluoromethoxy, chlorodifluoromethoxy, dichlorofluoromethoxy, 1,1,2,2-tetrafluoroethoxy, 1,2,2,2-tetrafluoroethoxy, 1,1,2,2-tetrachloroethoxy and 1,2,2,2-tetrachloroethoxy, cyano and nitro.

The compounds I can be obtained by the following method:

A 3(2H)-pyridazinone of the formula II and a compound of the formula III are reacted in the presence of a base at from −20° to 250° C., preferably from 20° to 120° C., in accordance with the equation below:

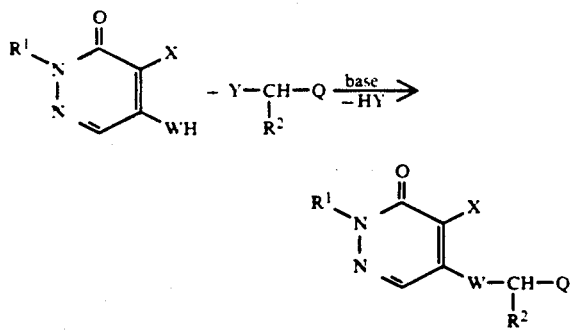

Some of the 3(2H)-pyridazinones of the general formula II are described in Belgian Patent 607 934, in EP-A-134 439, in Angew. Chem. 72 (1960) 864 et seq. and Chem. Pharm. Bull. 18 (1970) 147 et seq., or they can be prepared by the methods described therein.

The heterocycles are either known, and some of them are commercially available, or they can be prepared by conventional processes. Processes for the preparation of pyrazoles are to be found, for example, in: Heterocyclic Nitrogen Compounds, The Azoles, pp. 31 et seq., Cambridge University Press, 1976; for the preparation of imidazoles, for example, in: Advances in Heterocyclic Chem., Vol. 27, pp. 242 et seq., 1980; for the preparation of triazoles, for example, in: Comprehensive Heterocyclic Chemistry, A. R. Katritzky and C. W. Rees, Vol. 5, pp. 669 et seq., Pergamon Press, 1984; for the preparation of isothiazoles, oxazoles, thiazoles, oxadiazoles and thiadiazoles, for example in: Comprehensive Heterocyclic Chemistry, A. R. Katritzky and C. W. Rees, Vol. 6, pp. 131, 177, 235, 365, 447 et seq., Pergamon Press, 1984.

Y is a leaving group such as a sulfonyl radical or a halogen. Preferred sulfonyl radicals are methanesulfonyl, trifluoromethanesulfonyl, benzenesulfonyl and p-toluenesulfonyl, and preferred halogens are chlorine and bromine, and chlorine is particularly preferred.

To prepare the compounds I according to the invention by the method described above, the starting materials are normally used in the stoichiometric ratio. An excess of one of the components may be advantageous.

The reactions usually take place at adequate rates above −20° C. In general, 120° C. should not be exceeded. Since some of them take place with evolution of heat, it may be advantageous to provide means of cooling.

Normally, at least equivalent amounts of a base are added to II and/or III, but this can also be used in excess or as solvent. Examples of suitable bases are hydroxides of alkali metals and alkaline earth metals such as sodium hydroxide, potassium hydroxide and calcium hydroxide, alcoholates of alkali metals and alkaline earth metals such as sodium methylate, sodium ethylate, calcium methylate or potassium tert-butylate; alkali metal or alkaline earth metal hydrides; such as sodium hydride, potassium hydride or calcium hydride; alkali metal or alkaline earth metal carbonates such as sodium carbonate, potassium carbonate or calcium carbonate; aliphatic amines such as dimethylamine, triethylamine or diisopropylamine; heterocyclic amines such as piperidine, piperazine or pyrrolidine; and aromatic amines such as pyridine or pyrrole.

The reaction is expediently carried out in a solvent or diluent. Suitable examples are aliphatic hydrocarbons such as n-pentane, n-hexane, mixed hexane isomers and petroleum ether; halohydrocarbons such as chlorobenzene, methylene chloride, ethylene chloride, chloroform and tetrachloroethylene; aromatic hydrocarbons such as benzene, toluene, the xylenes and mixed isomers thereof; alcohols such as methanol, ethanol, n-propanol and isopropanol; ethers such as diethyl and di-n-butyl ethers, methyl tert-butyl ether, tetrahydrofuran and dioxane; ketones such as acetone, methyl ethyl ketone and methyl isopropyl ketone; nitriles such as acetonitrile and propionitrile; aprotic dipolar solvents such as dimethylformamide, dimethyl sulfoxide or pyridine. It is also possible to use mixtures of these substances as solvents and diluents.

The 3(2H)-pyridazinone of the formula II is expediently introduced into a diluent or solvent, followed by the starting material III. Conventional methods are used to isolate the novel compounds I. The products can be purified by recrystallization, extraction or chromatography.

To prepare salts which are tolerated by plants, the appropriate 3(2H)-pyridazinones I can be reacted with conventional agents for forming salts, such as hydrochloric acid, hydrobromic acid, hydroiodic acid, sulfuric acid, phosphoric acid, formic acid, acetic acid, oxalic acid, benzenesulfonic acid, p-toluenesulfonic acid, dodecylbenzenesulfonic acid, methyl chloride, methyl bromide, methyl iodide, ethyl chloride, ethyl bromide, ethyl iodide, n-propyl chloride, n-propyl bromide, dimethyl sulfate and diethyl sulfate at from 0° to 150° C., preferably from 20° to 120° C.

The reaction is expediently carried out in a solvent or diluent. Suitable examples are aliphatic hydrocarbons such as n-pentane, n-hexane, mixed hexane isomers and petroleum ether; aromatic hydrocarbons such as benzene, toluene, the xylenes and mixed isomers thereof; ethers such as diethyl ether, di-n-butyl ether, methyl tert-butyl ether, tetrahydrofuran and dioxane; ketones such as acetone, methyl ethyl ketone and methyl isopropyl ketone; halohydrocarbons such as chlorobenzene, methylene chloride, ethylene chloride, chloroform and tetrachloroethylene. It is also possible to use mixtures of these substances as solvents.

To prepare salts of suitable compounds I by the method described above, the starting materials are normally used in the stoichiometric ratio. However, it is perfectly possible that an excess of one of the components is advantageous.

The reactions usually take place at adequate rates above 0° C. In general, 120° C. should not be exceeded. Since some of them take place with evolution of heat, it may be advantageous to provide means of cooling.

Conventional methods are employed to isolate the salts of the compounds I according to the invention. The products obtained can be purified by recrystallization, extraction or chromatography.

The 3(2H)-pyridazinone derivatives of the formula I are suitable for effectively combating pests such as insects, arachnida, nematodes and snails. They may also be used as pesticides for protecting crop plants, and in the hygiene, stores protection and veterinary sectors.

Examples of injurious insects from the Lepidoptera order are *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Cho-* ristoneura fumiferana, Choristoneura occidentalis, Cirphis unipuncta, Cydia pomonella, Dendrolimus pini, Diaphania nitidalis, Diatraea grndiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis.

Examples from the Coleoptera order are Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and Sitophilus granaria.

Examples from the Diptera order are Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa.

Examples from the Thysanoptera order are Frankliniella fusca, Frankliniella occidentalis, Frankliniella tritici, Scirtothrips citri, Thrips oryzae, Thrips palmi and Thrips tabaci.

Examples from the Hymenoptera order are Athalia rosae, Atta cephalotes, Atta sexdens, Atta texana, Hoplocampa minuta, Hoplocampa testudinea, Monomorium pharaonis, Solenopsis geminata and Solenopsis invicta.

Examples from the Heteroptera order are Acrosternum hilare, Blissus leucopterus, Cyrtopeltis notatus, Dysdercus cingulatus, Dysdercus intermedius, Eurygaster integriceps, Euchistus impictivetris, Leptoglossus phyllopus, Lygus lineolaris, Lygus pratensis, Nezara viridula, Piesma quadrata, Solubea insularis and Thyanta perditor.

Examples from the Orthoptera order are Forficula auricularia, Acheta domestica, Gryllotalpa gryllotalpa, tachycines asynamorus, Locusta migratoria, Stauronotus meroccanus, Schistocerca peregrina, Nomadacris septemfasciata, Melanoplus spretus, Melanoplus femur-rubrum, Blatta orientalis, Blattella germanica, Periplaneta americana and Blabera gigantea.

Examples from the Arachnida order are Ixodes ficinus, Ornithodorus, moubata, Amblyomma americanum, Dermacentor silvarum, Boophilus microplus, Tetranychus telarius, Tetranychus pacificus, Paratetranychus pilosus, Bryobia praetiosa.

Examples from the Nemathelminthes class are rootknot nematodes, such as Meloidogyne hapla, Meloidogyne incognita, Meloidogyne javanica, cystforming nematodes, e.g., Globodera rostochiensis, Heterodera avenae, Hetrodera glycinae, Heterodera schatii, Hetrodera triflolii, and stem and leaf eelworms, such as Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Paratylenchus neglectus, Paratylenchus penetrans, Paratylenchus curvitatus, and Paratylenchus goodeyi.

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated napthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dust and broadcasting agents may be prepared by mixing or grinding the active ingredients with a solid carrier.

Examples of formulations are given below.

I. 5 parts by weight of compound no. 10 is intimately mixed with 95 parts by weight of particulate kaolin. A dust is obtained containing 5% by weight of the active ingredient.

II. 30 parts by weight of compound no. 50 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 83 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 10 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 50 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas; and vegetable products such as grain flours, bark meal, wood meal, and nutshell meal, cellulosic powders, etc.

The formulations generally contain from 0.1 to 95, and preferably 0.5 to 90, % by weight of active ingredient.

The active ingredient concentrations in the finished formulations may vary over a wide range. Generally, they are from 0.0001 to 10, and preferably from 0.01 to 1, %.

The active ingredients may also successfully be used in the ultra-low-volume (ULV) method, where it is possible to apply formulations containing more than 95 wt % of active ingredient, or even the active ingredient without additives.

In the open, the amount of active ingredient applied is for example from 0.02 to 10, particularly from 0.1 to 2, kg/ha.

The agents according to the invention also have pronounced molluscicidal properties both in slugs and snails, and are excellently suitable for combating snails in agricultural and horticultural crops.

In accordance with the invention, a preparation formulated for example as a broadcasting agent and effective against snails is obtained by employing an effective amount of 3(2H)-pyridazinone derivatives I.

Suitable formulations are described for instance in GB 2,087,723 and EP 190,595. They generally contain a bait, a binder, preservatives, dyes, pheromones, fillers, repellants, water, organic solvents, surfactants and the active ingredient.

As bait, any compound conventionally employed for this purpose may be used. It is preferred to use ground cereals such as wheat meal, coarsely ground wheat, barley and soybeans, bran, rice starch, fish meal, meat meal and molasses. The agent may contain just one bait, or a mixture of several.

Suitable binders are all those conventionally used for such purposes. Examples of preferred binders are methylcellulose, sugar, dextrin, starch, alginates, glycols, polyvinylpyrrolidone, lignin sulfonate, gum arabic, polyvinyl alcohol and polyvinyl acetate. The agent may contain one or several binders.

Examples of preservatives that may be employed are 2-hydroxybiphenyl, sorbic acid, p-hydroxybenzaldehyde, methyl p-hydroxybenzoate, benzaldehyde, benzoic acid, propyl p-hydroxybenzoate and p-nitrophenol.

Examples of dyes suitable as additives are inorganic pigments such as iron oxide, titanium dioxide and iron blue, and organic dyes such as anthraquinone, azo and metal phthalocyanine dyes.

Suitable substances acting as attractants on soil pests are all those conventionally used for this purpose. Examples are aniseed and aniseed oil.

Suitable fillers are all substances conventionally used for this purpose. Preferred fillers are kaolins, diatomaceous earth, talc, chalk and quartz powder.

Suitable substances exhibiting a repellant action on warmblooded animals such as dogs and hedgehogs are all components conventionally used for this purpose. Nonyl vanillylamide may be mentioned by way of example.

Suitable organic solvents are all those conventionally used for the manufacture of baits. It is preferred to use low-boiling organic solvents such as methanol, ethanol, butanol and methylene chloride.

Suitable surfactants are non-ionic active ingredients such as condensation products of polyalkylene oxides and alkylphenols and fatty acid polyoxyalkylene esters, e.g., octylphenoxypolyoxyethanol; cationic active ingredients such as quaternary ammonium salts, e.g., cetyl trimethylammonium chloride and cetyl pyridinium chloride, and anionic active ingredients such as the sodium salts of long-chain alkyl sulfates, e.g., sodium lauryl sulfate, salts of alkylaryl sulfates, the sodium salt of desoxycholic acid, the sodium salt of taurocholic acid and the sodium salt of tauroglycocholic acid.

Another preferred application form is seed dressing with a formulation conventionally employed for dressings.

The amount of active ingredient in the various application forms may vary within wide limits, e.g., from 0.001 to 90, especially from 0.5 to 50, and preferably from 1 to 10%, wt % in granular formulations and from 10 to 90 wt % in seed dressings.

The molluscicidal action of the agents according to the invention extends to both land and amphibious snails, e.g., from the genera Deroceras (Agriolimax), Limax, Helix, Helicogona, Cepaea, Milax, Lymnaea (Galba), Achatina, Theba, Cochlicella, Helicarion and Vaginulus. Examples of snails which cause damage are the slugs *Arion ater, A. lusitanicus, A. hortensis, Agriolimax reticulatus, Limax flavus, L. maximus, Milax gagates, Mariella dursumierei, Helicarion salius, Vaginula hedleyi* and *Pamarion pupillaris*, and the snails *Helix aspersa* spp., *cepaea nemoralis, Theba pisana, Achatina fulica, A. zanzibarica,* Bradybaena spp., Cochlodina spp., Helicella spp. and Euomphalia spp.

FORMULATION EXAMPLE VI 2 kg of compound no. 10, 8 kg of calcium stearate, 0.2 kg of sodium benzoate, 20 kg of chalk, 0.5 kg of blue dye and 63.3 kg of wheat bran were mixed in a mixer. This mixture was then moistened with sufficient water and kneaded in a kneader. The moist mixture was processed in an extruder to snail bait granules having a diameter of 3 mm, and dried at a maximum temperature of 60° C.

FORMULATION EXAMPLE VII

To prepare a seed dressing the following compounds were mixed:

480 g of compound no. 10
20 g of a commercial phenolsulfonic acid-urea-formaldehyde condensate
40 g of an ethylene-propylene block copolymer having a molecular weight of 10,000
2 g of xanthane rubber
0.5 g of Rhodamin FB
80 g of 1,2propylene glycol
5 g of silicone antifoam and water was added to make up 1 liter.

There may be added to the active ingredients (if desired, immediately before use (tankmix)) oils of various types, herbicides, fungicides, other pesticides and bactericides. These agents may be added to the agents according to the invention in a weight ratio of from 1:10 to 10:1.

MANUFACTURING EXAMPLES

Example 1

2-tert-butyl-4-chloro-5-[(4,5-dichloroimidazol-1-yl)-methylthio]-3(2H)-pyridazinon-3-one (compound no. 10)

At room temperature (about 20° C.), 7 g (0.038 mol) of 1-chloromethyl-4,5-dichloroimidazole in 30 ml of anhydrous dimethylformamide is dripped into 8.3 g (0.038 mol) of 2-tert-butyl-4-chloro-5-mercapto-3(2H)-pyridazin-3-one and 5.2 g (0.038 mol) of potassium carbonate in 50 ml of anhydrous dimethylformamide. The mixture is then stirred for 4 hours at 60° C., and overnight at room temperature (about 20° C.). The mixture is then poured into 200 ml of ice water and the solid which precipitates out is removed by suction filtration. Recrystallization from n-hexane/ethyl acetate (10:1) gives 10.8 g (77.5% of theory) of 2-tert-butyl-4-chloro-5-[(4,5-dichloroimidazol-1-yl)-methylthio]-3(2H)-pyridazinon-3-one as a pale powder of m.p. 161°-164° C.

Example 2

2-tert-butyl-4-chloro-5-[(5-methyl-1,3,4-thiadiazol-2-yl)-methylthio]-3(2H)-pyridazin-3-one (compound no. 50)

At room temperature (about 20° C.), 8.17 g (0.055 mol) of 2-chloromethyl-5-methyl-1,3,4-thiadiazole in 50 ml of anhydrous dimethylformamide is dripped into 12 g (0.055 mol) of 2-tert-butyl-4-chloro-5-mercapto-3(2H)-pyridazin-3-one and 7.6 g (0.055 mol) of potassium carbonate in 100 ml of anhydrous dimethylformamide. The mixture is then stirred for 2 hours at 80° C., and overnight at room temperature (about 20° C.). The mixture is then poured into 300 ml of ice water, followed by extraction with three times 100 ml of ethyl acetate. The combined ethyl acetate phases are dried over magnesium sulfate. After the solvent has been stripped off, the residue is recrystallized from n-hexane/ethyl acetate (6:1). There is obtained 8.4 g (46.2% of theory) of 2-tert-butyl-4-chloro-5[(5-methyl-1,3,4-thiadiazol-2-yl)-methylthio]-3(2H)-pyridazin-3-one as a colorless powder of m.p. 163°-165° C.

Example 3

2-tert-butyl-4-chloro-5-[(3-phenyl-1,2,4-oxadiazol-5-yl)-methylthio]-3(2H)-pyridazin-3-one (compound no. 83)

At room temperature (about 20° C.), 4.5 g (0.023 mol) of 5-chloromethyl-3-phenyl-1,2,4-oxadiazole in 30 ml of anhydrous dimethylformamide is dripped into 5.1 g (0.023 mol) of 2-tert-butyl-4-chloro-5-mercapto-3(2H)-pyridazin-3-one and 3.17 g (0.023 mol) of potassium carbonate in 50 ml of anhydrous dimethylformamide. The mixture is then stirred for 2 hours at 80° C., and overnight at room temperature (about 20° C.). It is then poured into ice water and extracted three times, each time with 100 ml of ethyl acetate. The organic phases are dried over magnesium sulfate and the solvent is evaporated under reduced pressure. Recrystallization from n-hexane/ethyl acetate (6:1) gives 5.7 g (66% of theory) of 2-tert-butyl-4-chloro-5-[(3-phenyl-1,2,4-oxadiazol-5-yl)-methylthio]-3(2H)-pyridazin-3-one as a colorless powder of m.p. 141°-143° C.

The compounds described in the table below may be prepared in accordance with these directions. The substitution positions on the heterocyclic structures are indicated by a line.

The compounds I given in the table without any physical data may be readily obtained from the corresponding precursors and are expected to have a similar action.

TABLE

3(2H)-Pyridazinone derivatives I

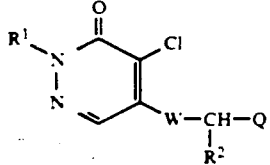

(I)

| No. | R¹ | R² | W | Q | Phys. data IR absorptions [cm⁻¹] or mp. [°C.] |
|---|---|---|---|---|---|
| 1 | CH₃ | H | S | 1-methylpyrazol-3-yl | |
| 2 | i-C₃H₇ | H | S | 1-methylpyrazol-3-yl | |
| 3 | t-C₄H₉ | H | S | 1-methylpyrazol-3-yl | 126–129 |
| 4 | t-C₄H₉ | CH₃ | S | 1-methylpyrazol-3-yl | |
| 5 | CH₃ | H | S | 1-methylimidazol-5-yl | |
| 6 | t-C₄H₉ | H | S | 1-methylimidazol-5-yl | |
| 7a | CH₃ | H | S | 4,5-dichloro-1-methylimidazol-2-yl | |
| 7b | CH₃ | H | O | 4,5-dichloro-1-methylimidazol-2-yl | 142 |
| 8 | i-C₃H₇ | H | S | 4,5-dichloro-1-methylimidazol-2-yl | |
| 9 | t-C₄H₉ | H | O | 4,5-dichloro-1-methylimidazol-2-yl | |
| 10 | t-C₄H₉ | H | S | 4,5-dichloro-1-methylimidazol-2-yl | 161–164 |

TABLE-continued
3(2H)-Pyridazinone derivatives I
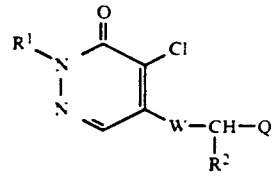
(I)
| No. | R¹ | R² | W | Q | Phys. data IR absorptions [cm⁻¹] or mp. [°C.] |
|---|---|---|---|---|---|
| 11 | t-C₄H₉ | CH₃ | S | N-methyl-dichloroimidazolyl | |
| 12 | CH₃ | H | S | triazolyl | |
| 13 | i-C₃H₇ | H | S | triazolyl | |
| 14 | t-C₄H₉ | H | S | triazolyl | 115–117 |
| 15 | CH₃ | H | S | triazolyl | |
| 16 | CH₃ | CH₃ | S | triazolyl | |
| 17 | i-C₃H₇ | H | S | triazolyl | |
| 18 | t-C₄H₉ | H | O | triazolyl | |
| 19 | t-C₄H₉ | CH₃ | S | triazolyl | |
| 20 | t-C₄H₉ | H | S | triazolyl | 84–88 |

TABLE-continued
3(2H)-Pyridazinone derivatives 1 (I)
| No. | R¹ | R² | W | Q | Phys. data IR absorptions [cm⁻¹] or mp. [°C.] |
|---|---|---|---|---|---|
| 21 | t-C₄H₉ | H | S | 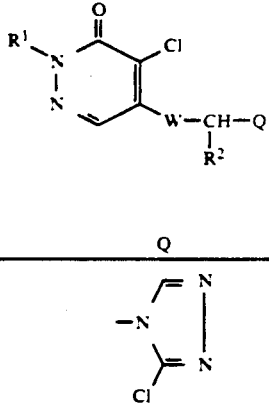 | 130–136 |
| 22 | t-C₄H₉ | CH₃ | S | 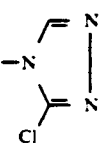 | |
| 23 | t-C₄H₉ | H | O | 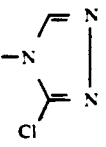 | |
| 24 | i-C₃H₇ | H | S | 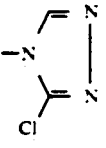 | |
| 25 | CH₃ | H | S | 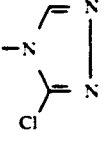 | |
| 26 | t-C₄H₉ | H | S | 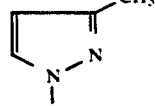 | |
| 27 | t-C₄H₉ | H | S | 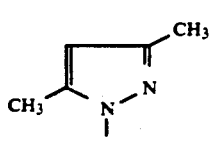 | |
| 28 | t-C₄H₉ | H | S | 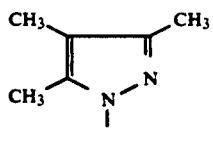 | |
| 29 | CH₃ | H | S | 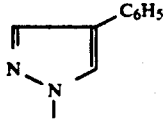 | |

TABLE-continued
3(2H)-Pyridazinone derivatives I
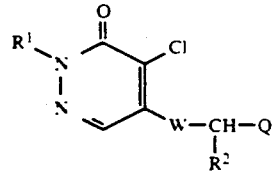
(I)
| No. | R¹ | R² | W | Q | Phys. data IR absorptions [cm⁻¹] or mp. [°C.] |
|---|---|---|---|---|---|
| 30 | i-C₃H₇ | H | S | 4-C₆H₅-pyrazol-1-yl | |
| 31 | t-C₄H₉ | H | S | 4-C₆H₅-pyrazol-1-yl | |
| 32 | t-C₄H₉ | CH₃ | S | 4-C₆H₅-pyrazol-1-yl | |
| 33 | t-C₄H₉ | H | S | 1-C₆H₅-pyrazol-5-yl | 86–89 |
| 34 | t-C₄H₉ | H | S | 1-(4-CH₃-C₆H₄)-pyrazol-4-yl | 111–114 |
| 35 | t-C₄H₉ | H | S | 1-(4-Br-C₆H₄)-pyrazol-4-yl | 163–165 |
| 36 | CH₃ | H | S | 2-C₆H₅-imidazol-1-yl | |
| 37 | i-C₃H₇ | H | S | 2-C₆H₅-imidazol-1-yl | |
| 38 | t-C₄H₉ | H | S | 2-C₆H₅-imidazol-1-yl | |

TABLE-continued

3(2H)-Pyridazinone derivatives I

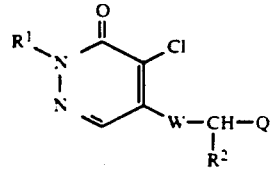

(I)

| No. | R¹ | R² | W | Q | Phys. data IR absorptions [cm⁻¹] or mp. [°C.] |
|---|---|---|---|---|---|
| 39 | t-C₄H₉ | H | S | (1-methyl-pyrazol-5-yl with CH₃) | |
| 40 | CH₃ | H | S | (1-methyl-pyrazol-5-yl with C₆H₅) | |
| 41 | i-C₃H₇ | H | S | (1-methyl-pyrazol-5-yl with C₆H₅) | |
| 42 | t-C₄H₉ | H | S | (1-methyl-pyrazol-5-yl with C₆H₅) | |
| 43 | t-C₄H₉ | CH₃ | S | (1-methyl-pyrazol-5-yl with C₆H₅) | |
| 44 | CH₃ | H | S | (1-methyl-triazole with CH₃, CH₃) | |
| 45 | i-C₃H₇ | H | S | (1-methyl-triazole with CH₃, CH₃) | |
| 46 | t-C₄H₉ | H | S | (1-methyl-triazole with CH₃, CH₃) | |
| 47 | t-C₄H₉ | CH₃ | S | (1-methyl-triazole with CH₃, CH₃) | |

TABLE-continued
3(2H)-Pyridazinone derivatives I
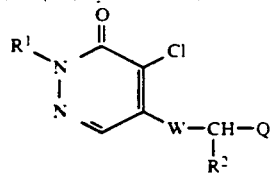
(I)
| No. | R¹ | R² | W | Q | Phys. data IR absorptions [cm⁻¹] or mp. [°C.] |
|---|---|---|---|---|---|
| 48 | CH₃ | H | S | (N═N, S, CH₃) | |
| 49 | i-C₃H₇ | H | S | (N═N, S, CH₃) | |
| 50 | t-C₄H₉ | H | S | (N═N, S, CH₃) | 163–165 |
| 51 | t-C₄H₉ | H | O | (N═N, S, CH₃) | |
| 52 | t-C₄H₉ | H | S | (N═N, S, C₂H₅) | |
| 53 | t-C₄H₉ | H | S | (N═N, S, cyclopropyl) | |
| 54 | CH₃ | H | S | (N═N, S, C₆H₅) | |
| 55 | i-C₃H₇ | H | S | (N═N, S, C₆H₅) | |
| 56 | t-C₄H₉ | H | S | (N═N, S, C₆H₅) | |
| 57 | t-C₄H₉ | CH₃ | S | (N═N, S, C₆H₅) | |
| 58 | CH₃ | H | S | (N═N, S, 4-Cl-C₆H₄) | |
| 59 | i-C₃H₇ | H | S | (N═N, S, 4-Cl-C₆H₄) | |

TABLE-continued

3(2H)-Pyridazinone derivatives I

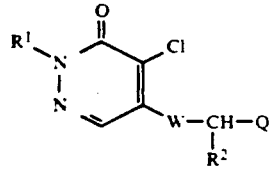

(I)

| No. | R¹ | R² | W | Q | Phys. data IR absorptions [cm⁻¹] or mp. [°C.] |
|---|---|---|---|---|---|
| 60 | t-C₄H₉ | H | S | (N=N ring with S, CH₃ and 4-Cl-C₆H₄ substituents) | 161–163 |
| 61 | CH₃ | H | S | (N=N ring with O, CH₃ and C₂H₅ substituents) | |
| 62 | i-C₃H₇ | H | S | (N=N ring with O, CH₃ and C₂H₅ substituents) | |
| 63 | t-C₄H₉ | H | S | (N=N ring with O, CH₃ and C₂H₅ substituents) | 123–124 |
| 64 | CH₃ | H | S | (N=N ring with O, CH₃ and cyclopropyl substituents) | |
| 65 | i-C₃H₇ | H | S | (N=N ring with O, CH₃ and cyclopropyl substituents) | |
| 66 | t-C₄H₉ | H | S | (N=N ring with O, CH₃ and cyclopropyl substituents) | |
| 67 | CH₃ | H | S | (N=N ring with O, CH₃ and C₆H₅ substituents) | |
| 68 | i-C₃H₇ | H | S | (N=N ring with O, CH₃ and C₆H₅ substituents) | |
| 69 | t-C₄H₉ | H | S | (N=N ring with O, CH₃ and C₆H₅ substituents) | 163–166 |
| 70 | t-C₄H₉ | CH₃ | S | (N=N ring with O, CH₃ and C₆H₅ substituents) | |

TABLE-continued
3(2H)-Pyridazinone derivatives I
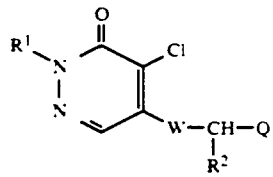
(I)
| No. | R¹ | R² | W | Q | Phys. data IR absorptions [cm⁻¹] or mp. [°C] |
|-----|----|----|----|----|-----|
| 71 | t-C₄H₉ | H | O | N=N, C(CH₃)=, O, C(C₆H₅)= | |
| 72 | CH₃ | H | S | N=N, C(CH₃)=, O, C(4-Cl-C₆H₄)= | |
| 73 | i-C₃H₇ | H | S | N=N, C(CH₃)=, O, C(4-Cl-C₆H₄)= | |
| 74 | t-C₄H₉ | H | S | N=N, C(CH₃)=, O, C(4-Cl-C₆H₄)= | 128–130 |
| 75 | t-C₄H₉ | CH₃ | S | N=N, C(CH₃)=, O, C(4-Cl-C₆H₄)= | |
| 76 | CH₃ | H | S | N=N, C(CH₃)=, O, C(4-F-C₆H₄)= | |
| 77 | i-C₃H₇ | H | S | N=N, C(CH₃)=, O, C(4-F-C₆H₄)= | |
| 78 | t-C₄H₉ | H | S | N=N, C(CH₃)=, O, C(4-F-C₆H₄)= | |
| 79 | t-C₄H₉ | CH₃ | S | N=N, C(CH₃)=, O, C(4-F-C₆H₄)= | |

TABLE-continued

3(2H)-Pyridazinone derivatives I (I)

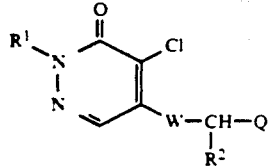

| No. | R¹ | R² | W | Q | Phys. data IR absorptions [cm⁻¹] or mp. [°C.] |
|---|---|---|---|---|---|
| 80 | t-C₄H₉ | H | O | (N=N, C(CH₃), O, C-4-fluorophenyl) | |
| 81 | CH₃ | H | S | (N, C(CH₃), O, N, C(C₆H₅)) oxadiazole | |
| 82 | i-C₃H₇ | H | S | (N, C(CH₃), O, N, C(C₆H₅)) oxadiazole | |
| 83 | t-C₄H₉ | H | S | (N, C(CH₃), O, N, C(C₆H₅)) oxadiazole | 141–143 |
| 84 | CH₃ | H | S | (N—O, C(CH₃), N, C(C₆H₅)) oxazole | |
| 85 | i-C₃H₇ | H | S | (N—O, C(CH₃), N, C(C₆H₅)) oxazole | |
| 86 | t-C₄H₉ | H | S | (N—O, C(CH₃), N, C(C₆H₅)) oxazole | |
| 87 | t-C₄H₉ | CH₃ | S | (N—O, C(CH₃), N, C(C₆H₅)) oxazole | |
| 88 | t-C₄H₉ | H | O | (N—O, C(CH₃), N, C(C₆H₅)) oxazole | |
| 89 | CH₃ | H | S | (C(CH₃), S, N, C(C₆H₅)) isothiazole | |
| 90 | i-C₃H₇ | H | S | (C(CH₃), S, N, C(C₆H₅)) isothiazole | |
| 91 | t-C₄H₉ | H | S | (C(CH₃), S, N, C(C₆H₅)) isothiazole | |

TABLE-continued

3(2H)-Pyridazinone derivatives I

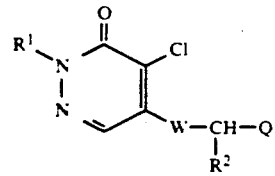

(I)

| No. | R¹ | R² | W | Q | Phys. data IR absorptions [cm⁻¹] or mp. [°C.] |
|---|---|---|---|---|---|
| 92 | t-C₄H₉ | CH₃ | S | (isothiazole, C₆H₅) | |
| 93 | t-C₄H₉ | H | O | (isothiazole, C₆H₅) | |
| 94 | CH₃ | H | S | (oxazole, C₆H₅) | |
| 95 | i-C₃H₇ | H | S | (oxazole, C₆H₅) | |
| 96 | t-C₄H₉ | H | S | (oxazole, C₆H₅) | |
| 97 | t-C₄H₉ | CH₃ | S | (oxazole, C₆H₅) | |
| 98 | t-C₄H₉ | H | O | (oxazole, C₆H₅) | |
| 99 | CH₃ | H | S | (thiazole, C₆H₅) | |
| 100 | i-C₃H₇ | H | S | (thiazole, C₆H₅) | |
| 101 | t-C₄H₉ | H | S | (thiazole, C₆H₅) | 1649, 1563, 1326, 1212 |
| 102 | t-C₄H₉ | CH₃ | S | (thiazole, C₆H₅) | |
| 103 | CH₃ | H | S | (thiazole, 4-Cl-C₆H₄) | |

TABLE-continued

3(2H)-Pyridazinone derivatives I

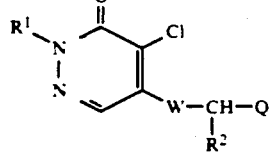

(I)

| No. | R¹ | R² | W | Q | Phys. data IR absorptions [cm⁻¹] or mp. [°C.] |
|---|---|---|---|---|---|
| 104 | i-C₃H₇ | H | S | (2-methylthien-5-yl)=N-CH-(4-chlorophenyl) | |
| 105 | t-C₄H₉ | H | S | (2-methylthien-5-yl)=N-CH-(4-chlorophenyl) | 1647, 1562, 1495, 1398 |
| 106 | t-C₄H₉ | CH₃ | S | (2-methylthien-5-yl)=N-CH-(4-chlorophenyl) | |
| 107 | t-C₄H₉ | H | O | (2-methylthien-5-yl)=N-CH-(4-chlorophenyl) | |
| 108 | CH₃ | H | S | 2-methyl-4-phenylthiazol-5-yl | |
| 109 | i-C₃H₇ | H | S | 2-methyl-4-phenylthiazol-5-yl | |
| 110 | t-C₄H₉ | H | S | 2-methyl-4-phenylthiazol-5-yl | 128–131 |
| 111 | t-C₄H₉ | H | O | 2-methyl-4-phenylthiazol-5-yl | |
| 112 | CH₃ | H | S | 2-methyl-4-(4-chlorophenyl)thiazol-5-yl | |

TABLE-continued

3(2H)-Pyridazinone derivatives I

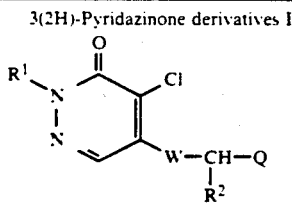

(I)

| No. | R¹ | R² | W | Q | Phys. data IR absorptions [cm⁻¹] or mp. [°C.] |
|---|---|---|---|---|---|
| 113 | i-C₃H₇ | H | S | (4-chlorophenyl-thiazoline with =C(CH₃)) | |
| 114 | t-C₄H₉ | H | S | (4-chlorophenyl-thiazoline with =C(CH₃)) | |
| 115 | t-C₄H₉ | H | O | (4-chlorophenyl-thiazoline with =C(CH₃)) | |
| 116 | t-C₄H₉ | H | S | (N-methyl imidazole with CH₂C₆H₅) | |
| 117 | t-C₄H₉ | CH₃ | S | (N-methyl imidazole with CH₂C₆H₅) | |
| 118 | t-C₄H₉ | H | S | (oxazole with C₆H₅) | |
| 119 | t-C₄H₉ | H | S | (oxazoline with CH₂C₆H₅) | |
| 120 | t-C₄H₉ | H | S | (oxazoline with C₆H₅) | |
| 121 | t-C₄H₉ | H | S | (4-methoxyphenyl-thiazoline with =C(CH₃)) | |

TABLE-continued

3(2H)-Pyridazinone derivatives I $$\begin{array}{c} R^1-N-N=CH-\underset{R^2}{C}H-Q \\ \text{(with C=O, Cl substituents)} \end{array} \quad (I)$$

| No. | $R^1$ | $R^2$ | W | Q | Phys. data IR absorptions [cm$^{-1}$] or mp. [°C.] |
|---|---|---|---|---|---|
| 122 | t-C$_4$H$_9$ | H | S | (thiazole-CH=C(3,4-Cl$_2$C$_6$H$_3$)) | |
| 123 | CH$_3$ | H | S | (thiazole-C(C$_6$H$_5$)=N) | |
| 124 | i-C$_3$H$_7$ | H | S | (thiazole-C(C$_6$H$_5$)=N) | |
| 125 | t-C$_4$H$_9$ | H | S | (thiazole-C(C$_6$H$_5$)=N) | |
| 126 | t-C$_4$H$_9$ | H | S | (thiazole-C(4-F-C$_6$H$_4$)=) | 104-109 |

USE EXAMPLES

In the following examples, the compounds according to the invention, or agents containing them, were investigated as to their action on *Tetranychus telarius, Caenorhabditis elegans, Plutella maculipennis* and *Dysdercus intermedius.*

The concentrations at which the compounds exhibit 100% kill or inhibition are the minimum concentrations. At least two experiments were run for each concentration.

The purity of the active ingredients was >95%. The formulation employed was a 0.1% acetonic solution or a 10 wt % aqueous emulsion concentrate obtained by adding the active ingredient to a mixture of 70 wt % of cyclohexanone, 20 wt % of Nekanil LN ® ($\triangleq$ Lutensol AP6, a spreader-sticker based on ethoxylated alkylphenols and having an emulsifying and dispersant action) and 10 wt % of Emulphor EL ® ($\triangleq$ Emulan El ®, an emulsifier based on ethoxylated fatty alcohols). The concentrations given in the examples were obtained by diluting the formulated active ingredient with water.

EXAMPLE A

*Tetranychus telarius* (Red Spider)

Potted bush beans exhibiting the second pair of true leaves are sprayed to runoff in a spray cabinet with aqueous formulations of the active ingredients. The plants are placed on a rotating table and are sprayed from all side with a total of 50 ml of spray liquior. The plants are under heavy mite attack and bear numerous eggs.

The action is assessed after 5 days by means of a binocular microscope. During this period, the plants are kept under normal greenhouse conditions.

In this experiment, compounds 34 and 101 had a good action.

EXAMPLE B

Contact Action on *Caenorhabditis elegans* (Nematodes)

0.5 ml of 0.1% acetonic active ingredient solutions are applied to the surface of a nutrient medium (5 ml in plastic Petri dishes 25 mm in diameter and 10 mm high). After the acetone has evaporated, the medium is infected with 30 ml of E coli bacteria and 50 ml of nematode suspension.

After 48 hours, the contact action was assessed in % kill. Compounds 34, 35 and 101 had a good action.

EXAMPLE C

Contact Action on *Plutella maculipennis* (Diamondback Moth)

Leaves of young cabbage plants are dipped for 3 seconds in aqueous formulations of the active ingredients and placed, after excess liquid has been briefly allowed to drip off, on a moist filter paper in a Petri dish. 10 caterpillars of the 4th stage are then placed on each leaf. The kill rate is assessed after 48 hours.

Compounds 20, 35 and 83 had a good action.

EXAMPLE D

Ovicidal Action on *Dysdercus intermedius*

Pieces of adhesive tape (about 0.8 cm) are stuck to the top edge of plastic plant markers. 24 hours before commencement of the experiment, eggs of the cotton stainer contained in a vessel are attached to the adhesive strips by dipping the markers into the vessel.

The eggs are then dipped for 5 seconds into aqueous formulations of the active ingredients and excess liquid is allowed to drip off onto filter paper.

The markers are placed (adhesive tape up) in plastic pallets which are covered with a glass plate. Care is taken during the experiment to provide sufficient moisture to prevent drying out.

Assessment takes place after about 8 days (after the larvae in the control batch have hatched).

In this experiment, compounds 14, 21 and 34 have a good action.

We claim:

1. A 3(2H)-pyridazinone compound of the formula I

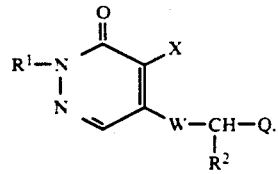

where $R^1$ is $C_1$-$C_8$-alkyl, $R^2$ is hydrogen or $C_1$-$C_4$-alkyl, X is halogen, W is oxygen or sulfur, and Q is a 5-membered heterocyclic radical selected from the group consisting of 1,2,4-oxadiazole, 1,3,4-oxadiazole, 1,2,4-thiadiazole, 1,3,4-thiadiazole, 1,2,4-triazole and 1,3,4-triazole, wherein the triazole radicals are linked via a nitrogen atom and the other heterocyclic radicals via a carbon atom, and which is unsubstituted or mono- to trisubstituted by halogen, $C_1$-$C_8$-alkyl, $C_2$-$C_6$-alkenyl, $C_2$-$C_4$-alkynyl, $C_1$-$C_4$-haloalkyl, $C_1$-$C_8$-alkoxy, $C_2$-$C_8$-alkoxyalkyl, $C_3$-$C_8$-cycloalkyl, cyano, nitro, phenyl, naphthyl or $C_7$-$C_{12}$-phenylalkyl which are unsubstituted or mono- to trisubstituted by halogen, $C_1$-$C_8$-alkyl, $C_1$-$C_8$-alkoxy, $C_1$-$C_4$-haloalkyl, $C_1$-$C_4$-haloalkoxy, cyano or nitro, and plant-tolerated salts thereof.

2. A pesticidal composition comprising an insecticidal, arachnidicidal, nematodicidal, or molluscicidal amount of a compound described in claim 1 and a plant-tolerated carrier therefor.

3. A pesticidal composition as described in claim 2 wherein the 3(2H)-pyridazinone compound is present in a concentration of 0.1 to 95 wt %.

4. A composition comprising an amount effective to kill snails of a 3(2H)-pyridozone compound described in claim 1 and a snail bait.

5. A process for combatting insects, arachnids, nematodes, or mollusks which comprises applying a composition as described in claim 2 to the insect, arachnid, nematode or mollusk or to an area which is to be kept free from said animals.

* * * * *